United States Patent [19]

Schroeder et al.

[11] 4,139,030
[45] Feb. 13, 1979

[54] AMALGAM DISPENSING DEVICE

[75] Inventors: Manfred F. Schroeder, Point Pleasant Beach; Joseph G. Biondo, Watchung, both of N.J.; Joseph Aliotta, Staten Island, N.Y.

[73] Assignee: Engelhard Minerals & Chemicals Corporation, Iselin, N.J.

[21] Appl. No.: 759,816

[22] Filed: Jan. 17, 1977

[51] Int. Cl.$^2$ ............................................. B65B 1/30
[52] U.S. Cl. ..................... 141/98; 141/100; 141/360; 221/96; 221/264; 222/307
[58] Field of Search ................. 221/96, 133, 264, 197; 222/153, 136, 137, 305-308, 361, 365, 340; 141/351, 352, 358, 360-362, 98-100, 105

[56] References Cited

U.S. PATENT DOCUMENTS

| | | | |
|---|---|---|---|
| 1,605,832 | 11/1926 | Garhart | 222/137 |
| 2,849,035 | 8/1958 | Morey | 141/360 |
| 3,168,213 | 2/1965 | De Gon | 221/96 |
| 3,271,011 | 9/1966 | Rohm et al. | 222/136 |
| 4,023,715 | 5/1977 | Biondo | 222/307 |

Primary Examiner—Allen N. Knowles
Assistant Examiner—H. Grant Skaggs
Attorney, Agent, or Firm—R. Jonathan Peters; Victor E. Libert; John E. Crowe

[57] ABSTRACT

A device for dispensing ingredients, such as the ingredients for a dental amalgam, has a handle portion and a head portion formed of mating parts with the handle angulated to the head and formed for convenient gripping by the user's hand. A slide mounted in the head slides laterally when pushed by the user's thumb to transport measured ingredients to a common aperture for delivery into a container. The container, when put in place, releases a latch that holds the slide normally in measuring position and prevents transport of the ingredients unless the container is in position to catch them.

Adjustment of a measuring chamber for liquid mercury, to accurately proportion it, is by a valve having an end projecting, more or less, into a chamber, so as to vary the volume of the chamber. The position of the valve is controlled by a rectilinearly movable cam whose position may be fixed by a lock nut which normally is inaccessible in a recess in the head portion.

12 Claims, 13 Drawing Figures

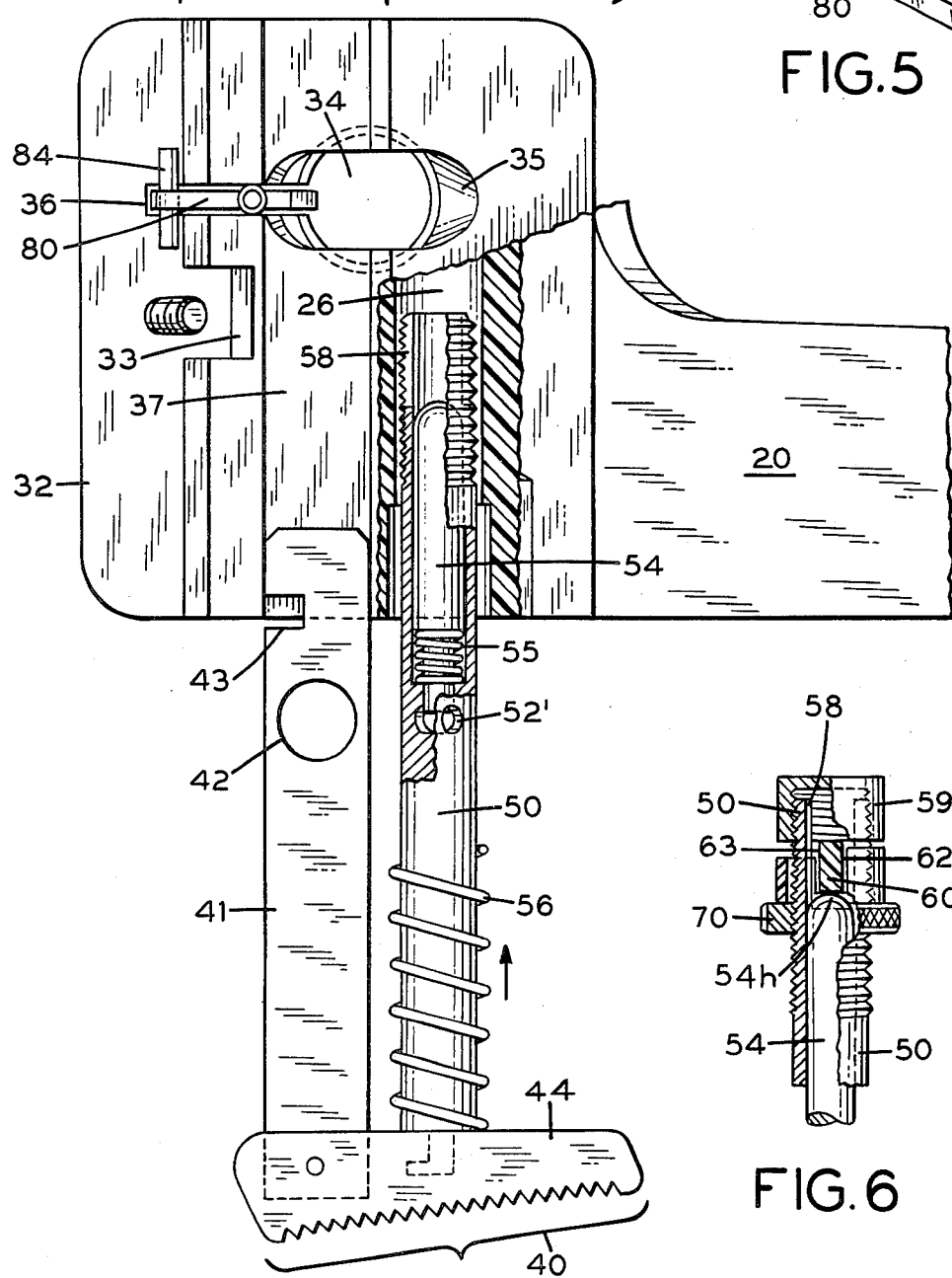

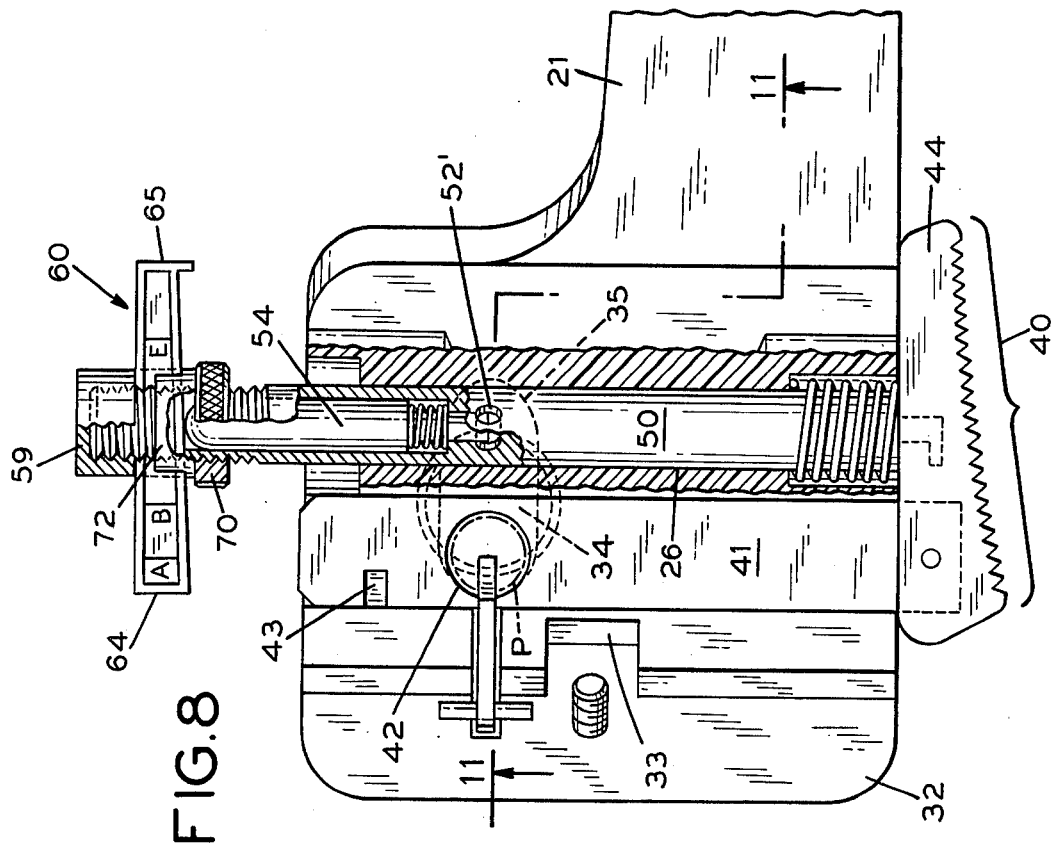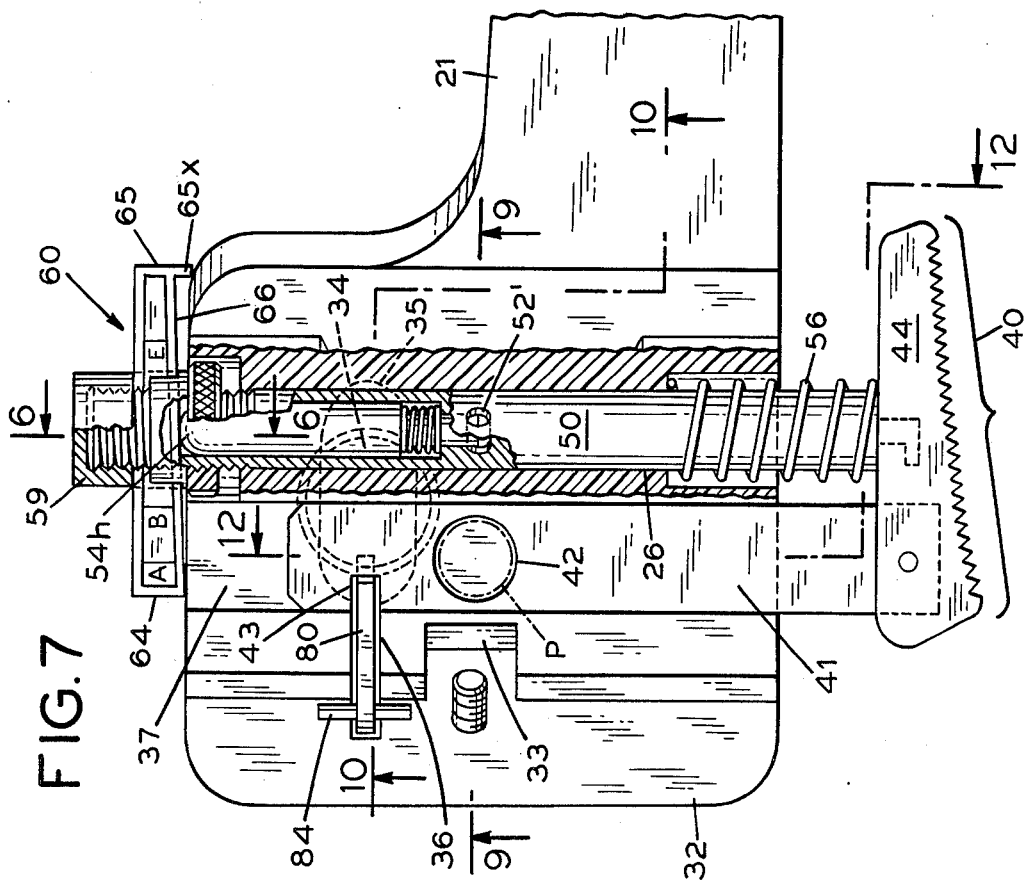

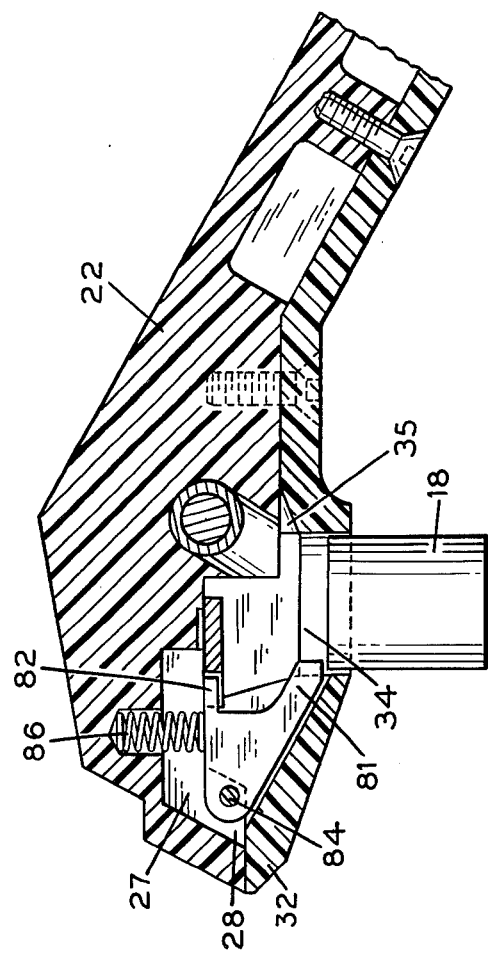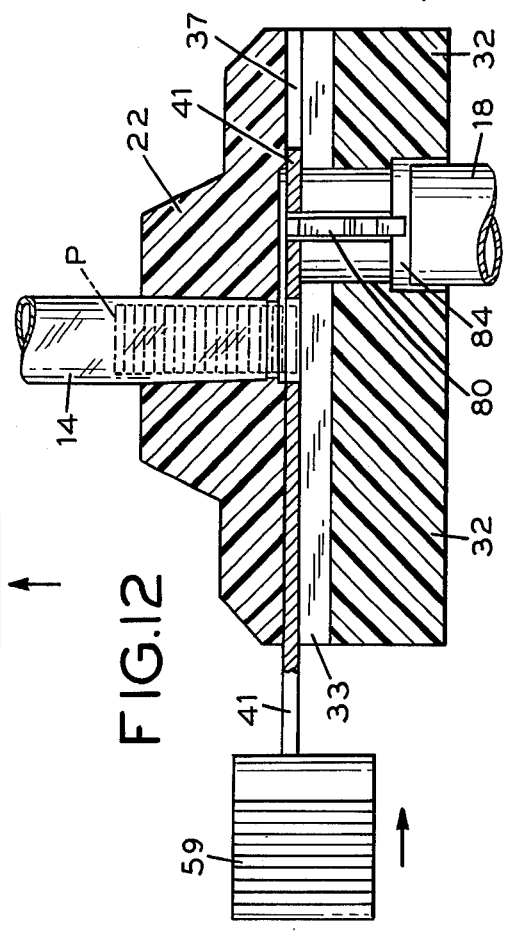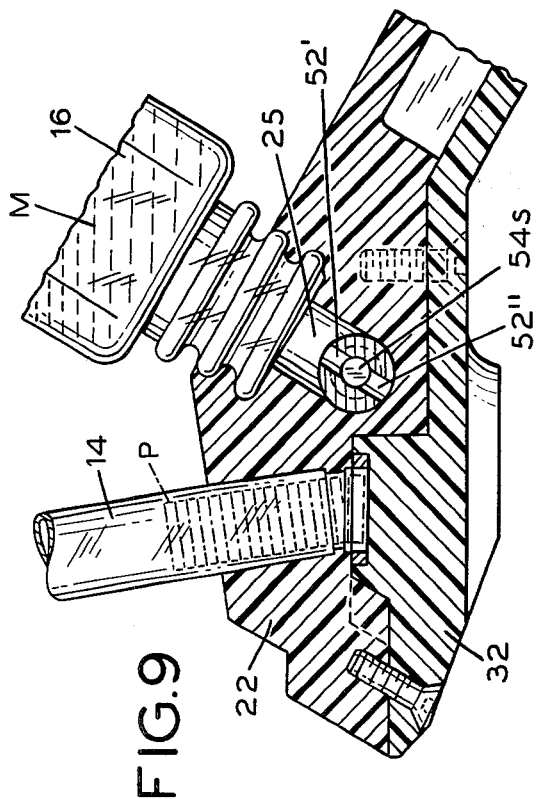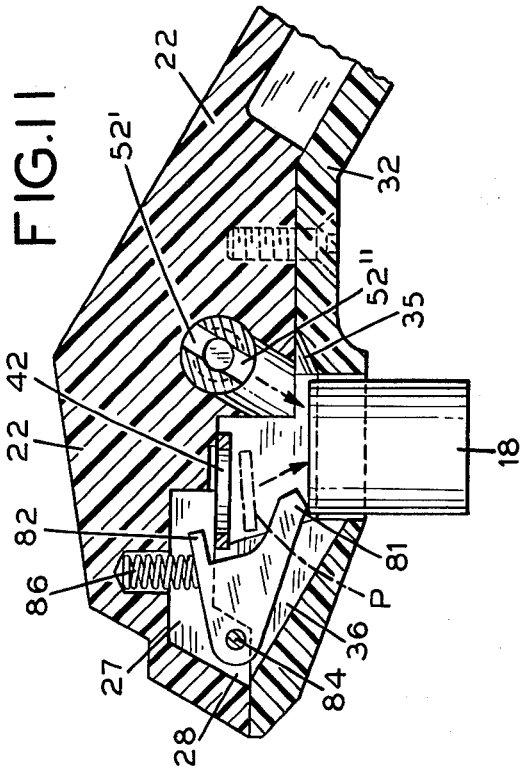

AMALGAM DISPENSING DEVICE

This invention relates to a device for dispensing and bringing together certain amounts of ingredients from two supply sources such as the ingredients of a dental amalgam, for example, premeasured amounts of silver alloy pellets and mercury, and delivering the mixture to a capsule or receptacle.

BACKGROUND OF THE INVENTION

Devices of the type to which this invention relates as heretofore known included a manually slidable member mounted in a body member that could be affixed to a wall or could be hand-held. On the body was a permanently mounted receptacle or cartridge for mercury and a removable or replaceable cartridge for silver alloy pellets. The slidable member in one position received a dosage of one pellet and a dosage of a predetermined adjustable amount of mercury. The permanent mercury reservoir was covered by a cap with an air vent hole which had to be kept closed during loading of the alloy pellets.

One example of such a prior device is disclosed in the De Gon U.S. Pat. No. 3,168,213 issued Feb. 2, 1965.

Among the disadvantages of such prior devices are liability of mercury spillage if the device was moved from horizontal upright position either inadvertently or purposely without closing the vent hole with a finger or in some other way; oxidation of the mercury through the vent hole; contamination of the working mechanism and parts by mercury oxidation; contamination of the finger used to close the vent hole when the device is moved from horizontal position; inability to lay the device on its side or place it upside down or tilt it in any plane during handling; liability of inadvertent or accidental operation of the device without a receiving capsule in place to catch the mercury and pellet, resulting in discharge on the floor.

SUMMARY OF THE INVENTION

In accordance with the present invention there is provided a dispensing and mixing device for liquid and solid ingredients comprising a body part having a cover part secured to it. A first passage is provided in the body part and is adapted to receive a liquid ingredient container. A second passage is provided in the body part and is adapted to receive a solid-ingredient container, and a guideway is located in the body part transversely with respect to the first passage. A channel is provided in the cover part and a measuring and dispensing assembly has solid-ingredient conveying means slidable in the channel and liquid-ingredient measuring and conveying means slidable in the guideway. A discharge port is in the cover part and is adapted to receive a receiving container in receiving position beneath the discharge port. The measuring and dispensing assembly is movable from a normal position to a discharge position to deliver both the solid and the liquid ingredients into the discharge port and into the associated receiving container in its receiving position beneath the discharge port. Locking means adapted to be disabled by the receiving container and preventing movement of the assembly to its discharge position, except when the receiving container is in its receiving position and disables said locking means, are also provided.

In accordance with one aspect of the invention, the locking means comprises a movable latch member normally in a locking position and engaging the assembly to prevent its movement, the latch member being engaged by the receiving container when the receiving container is in its receiving position to cause disengagement of the assembly by the latch.

In accordance with another aspect of the invention, an outwardly closed liquid container is mounted in the first passage and is adapted to contain a liquid ingredient therein. Means securing the body part and the cover part tightly together and sealing the associated liquid ingredient within the device while the assembly is in normal position and the liquid container is mounted are also provided. In this way, the device may be positioned in any position without spilling the liquid ingredient.

Certain advantages of the invention are achieved, in accordance with yet another aspect of the invention, by the provision of a dispensing and mixing device for liquid and solid ingredients comprising a body part having a cover part secured to it. A first passage is provided in the body part and is adapted to receive a liquid ingredient container. A second passage is provided in the body part and is adapted to receive a solid-ingredient container, and a guideway is located in the body part transversely with respect to the first passage. A channel is provided in the cover part and a measuring and dispensing assembly has solid-ingredient conveying means slidable in said channel and liquid-ingredient measuring and conveying means slidable in said guideway. A discharge port is in the cover part, and the assembly is movable from a normal position to a discharge position to deliver both the solid and the liquid ingredients into the discharge port. Measuring means for the liquid ingredient comprises a transverse passage in the liquid ingredient measuring and conveying means providing a measuring chamber. A longitudinal passage is in the liquid ingredient measuring and conveying means, one end of which connects with the measuring chamber. A valve member is mounted for rectilinear slidable movement in the longitudinal passage to vary the volume of the measuring chamber, and means are provided movable relative to and engaging the valve member and manually operable in one direction to decrease the volume of the chamber for controlling the volume of said measuring chamber. Means are also provided on the liquid ingredient conveying means to maintain the valve member in adjusted position, the body part having a recess receiving the means to maintain the valve member in adjusted position, inaccessibly in normal position of said assembly. The transverse passage connects with the liquid ingredient passage in the normal position and with the discharge port in the discharge position.

The means movable relative to and engaging the valve member may be a rectilinearly movable member having a cam surface engaging the valve member to move it.

The present invention provides a number of advantages, some of which are as follows. The invention provides a normally closed venting system (in contrast to the prior art open venting system) with venting through the system without a constantly open passage, whereby oxidation of the mercury is minimized and it is kept cleaner with the result that less frequent cleaning of the unit is required. Concomitantly the invention allows the device to be laid on its side, wall hung, placed upside down, or tilted in any plane during handling, without spillage of mercury.

The invention also includes means to lock the device against operation which is released only when a capsule or receptacle is put in place to catch the pellet and mercury, thereby preventing accidental operation and a discharge of the mercury and the capsule onto the floor.

Further the device provides universal vial loading with all current brand vials and pellet sizes and also the use of a screw-in type of disposable mercury cartridge.

Vernier-bar means is provided for accurate proportioning of the mercury from a baseline factory-set calibration, and visual reference over the full range of mercury ratios. A cam lock nut received in a recess provides tamper-proof setting of the selected mercury ratios, so that the manufacturer's recommended setting or one most suitable for the dentist is maintained without exposure of accidental or inadvertent change by the dentist or his assistants.

The advantages and objects of the invention will become apparent as it is described in connection with the accompanying drawings.

In the drawings:

FIG. 4 is an exploded plan view with about three-fourths of the head of the body broken away to show the slide assembly and valve details and to expose the inner surface of the cover head, and with the remaining lower left quadrant of the head broken away along a horizontal plane midway through the dispensing slide assembly.

FIG. 5 is a perspective view of the essential parts of the latch mechanism, of the device of FIGS. 1-4.

FIG. 6 is a fragmentary elevation view partly in section of the adjustment of the mercury proportioning means and its locking means, with the section taken along line 6—6 of FIG. 7.

FIG. 7 is a plan view of the device with the body broken away to show the slide assembly and valve details in latched position and to expose details of the inner surface of the cover.

FIG. 8 is a view similar to FIG. 7 with the slide assembly unlatched and pushed in to dispense the pellet and mercury.

FIG. 9 is a view taken along line 9—9 of FIG. 7.

FIG. 10 is a view taken along line 10—10 of FIG. 7.

FIG. 11 is a view taken along line 11—11 of FIG. 8.

FIG. 12 is a view taken along line 12—12 of FIG. 7.

Figure 1:
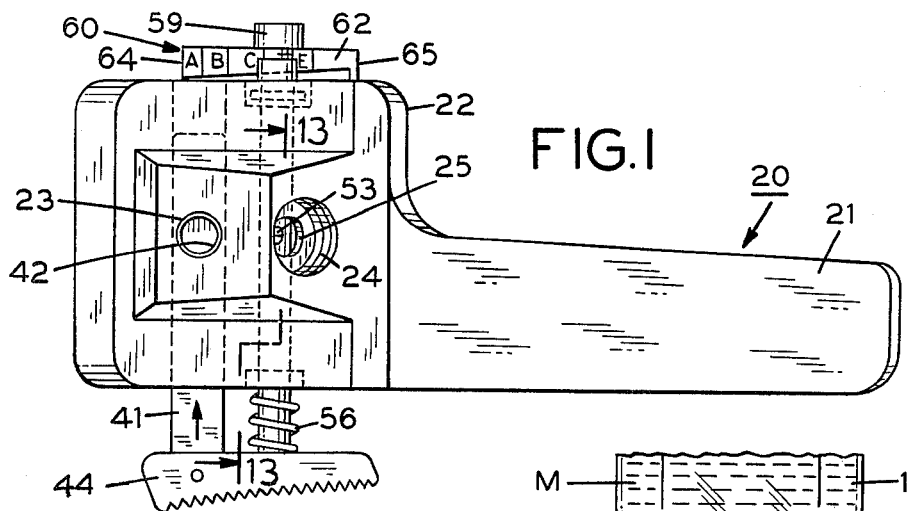
FIG. 1 is a plan view of a device embodying the invention.
Figures 2, 13:
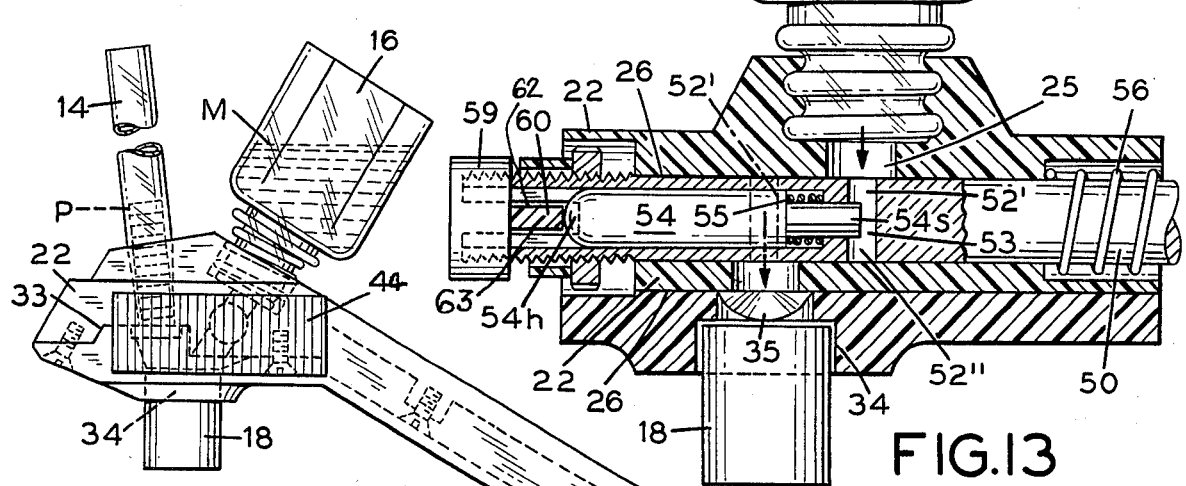
FIG. 2 is a side elevation view of the device of FIG. 1 with the mercury and pellet containers in place.
FIG. 13 is a view taken along line 13—13 of FIG. 1.
Figure 3:
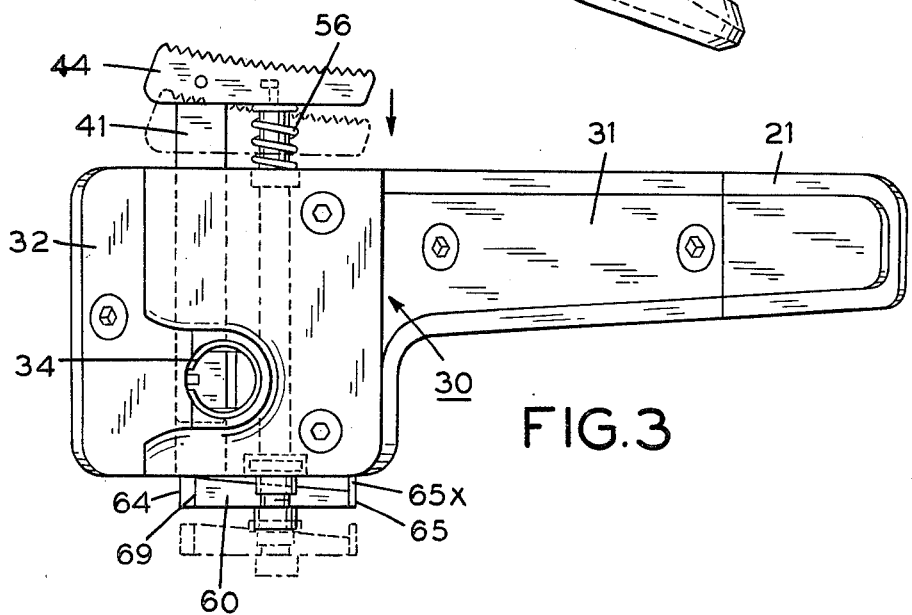
FIG. 3 is a bottom plan view of the device of FIGS. 1 and 2.

Referring to the drawings and particularly FIGS. 1-3, the invention is embodied in a device having a body part designated generally by 20 and a cover part designated generally by 30, both being preferably made of rigid synthetic plastic material. These two parts are of similar but not identical profile.

The body part 20 has an elongated handle portion 21, adapted to be grasped in the hand of the user, and a head portion 22 angulated to the handle at an obtuse angle of about 150° and enlarged laterally with respect to the handle portion.

The cover portion likewise has an elongated handle portion 31 and a head portion 32, the handle portion 31 being narrower than the body handle portion 21 and adapted to lie within an elongated recess in the handle 21 in such a way that the two handle portions cooperate to provide a smooth unitary handle for the device. Means securing body part 20 and cover part 30 tightly together are provided, in the illustrated embodiment, by the screws best shown in FIGS. 9, 10 and 11.

The head portion 22 of the body part has an internally screw-threaded, centrally located, circular opening 24 adapted to receive the screw-threaded neck of a non-metallic container or cartridge 16, usually glass or plastic, containing mercury. The opening 24 has a cylindrical passage 25 concentric therewith in its bottom which connects with a cylindrical passage or guideway 26 passing transversely through the head 22 from one side to the other. Slidably received in the guideway is a dispensing member or rod designated generally by 50, as will hereinafter be more fully described.

Passing through the head 22 adjacent the mercury passage 25 is a bore or cylindrical passage 23 adapted to receive a vial 14 containing pellets P of silver alloy or other material for forming an amalgam with mercury. The passage 23 and vial 16 are angulated at a narrow acute angle with respect to the mercury cartridge 16, to provide space between them.

Formed on the inner face of the cover member 30 is a flat-topped rib 33 which fits into a cooperating channel in the inner face of the head 22 of the body member. The rib 33 has a guide channel 37 extending lengthwise along its flat top to guide a pellet dispensing blade 41 as will hereinafter be more fully described. Along the channel toward one end, is an opening or discharge port 34 passing through the head 32 with an inclined gutter 35 (see FIG. 4) to guide mercury into the opening 34 as will hereinafter more fully appear.

The opening 24 is adapted to receive the neck or open mouth of a capsule or receptacle 18 for the pellet and mercury.

A slidable measuring and dispensing assembly including solid ingredient conveying means and liquid measuring and conveying means, designated generally by numeral 40, is provided for receiving and transporting the pellets P (shown in dotted lines in FIGS. 2, 7, 8, 9, 11 and 12) and mercury M, from the pellet vial 14 and mercury cartridge 16, respectively, within the device to the capsule 18. This assembly is shown partially inserted in the exploded view of FIG. 4.

The assembly comprises solid ingredient conveying means such as a flat bar or blade 41 having a notch 43 for a latch 80 as hereinafter described, and a circular aperture 42. The blade 41 slides in the aforementioned channel 37 which runs along the rib 33 as may be seen in FIGS. 4 and 7.

In FIG. 4 about three-quarters of the head 22 of the body 20 is broken away to show the inner face of the cover head 32, and the remainder of the head 22 is broken away along a horizontal plane (viewing device as positioned in FIG. 2) midway through a mercury dispensing rod 50, so as to show the details of the rod, as hereinafter described. The rod 50 and blade 41 are both affixed at their outer ends to a thumb piece 44 for manually operating the slide assembly.

In the normal or inactivated position (FIGS. 1 and 7) of the blade, its pellet aperture 42 is located in alignment with the vial aperture 23 so as to accept a pellet from the vial 14. The aperture is preferably of sufficient size to accommodate all currently known sizes of pellets used in dental work. The inner surface of the head 22 from the pellet vial opening 23 to a position over the discharge port 34 is countersunk to provide room for passage of the pellets.

and presses upon the bifurcation 82 urging it into the notch 43 in the pellet blade 41 (see FIGS. 7 and 10).

When the capsule is inserted in the hole 34 in the cover head 32, the capsule engages the lower bifurcation 81 of the latch and rotates it from locking position of FIGS. 7 and 10 into released position of FIG. 11 wherein the slide assembly is freed to be pushed from measuring into discharge position (FIG. 8).

From the foregoing, it will be noted that the device is assembled from parts which can be inexpensively manufactured and easily assembled. Moreover, without the use of screw-threaded parts, variation of the volume of the mercury measuring chamber can be quickly, easily and accurately made, whereby a device that is less expensive and more precise than heretofore is provided.

Modifications within the scope of the invention will occur to those skilled in the art. Therefore, the invention is not limited to the precise form and configuration disclosed.

I claim:

1. A dispensing and mixing device for liquid and solid ingredients comprising
   a body part and a cover part secured thereto,
   a first passage in said body part adapted to receive a liquid ingredient container,
   a second passage in said body part adapted to receive a solid-ingredient container,
   a guideway in said body part transversely located with respect to said first passage,
   a channel in said cover part,
   a measuring and dispensing assembly having solid-ingredient conveying means slidable in said channel and liquid-ingredient measuring and conveying means slidable in said guideway,
   a discharge port in said cover part adapted to receive a receiving container in receiving portion beneath said discharge port,
   said assembly being movable from a normal position to a discharge position to deliver both the solid and the liquid ingredients into said discharge port and into the associated receiving container in receiving position beneath said discharge port,
   locking means adapted to be disabled by said receiving container and preventing movement of said assembly to discharge position except when said receiving container is in receiving position and disables said locking means.

2. A device as claimed in claim 1 wherein said locking means comprises a movable latch member normally in a locking position engaging said assembly to prevent its movement, said latch member being engaged by the associated receiving container when the associated receiving container is in receiving position to cause disengagement of the assembly by the latch.

3. A device as claimed in claim 2 having means pivotally mounting said latch in the device, and spring means biasing the latch member into locking position.

4. A device as claimed in claim 2 wherein said solid ingredient conveying means has a notch in which said latch member is received in locking position.

5. A device as claimed in claim 4 wherein said solid ingredient conveying means is a bar member having an aperture for receiving the solid ingredient and having a notch in which said latch member is received in locking position.

6. A device as claimed in claim 1 further including
   an outwardly closed liquid container mounted in said first passage and adapted to contain a liquid-ingredient therein, and
   means securing said body part and said cover part tightly together and sealing the associated liquid ingredient within said device while said assembly is in normal position and said liquid container is mounted, whereby said device may be positioned in any position without spilling said liquid ingredient.

7. A dispensing and mixing device for liquid and solid ingredients comprising
   a body part and a cover part secured thereto,
   a first passage in said body part adapted to receive a liquid ingredient container,
   a second passage in said body part adapted to receive a solid-ingredient container,
   a guideway in said body part transversely located with respect to said first passage,
   a channel in said cover part,
   a measuring and dispensing assembly having solid-ingredient conveying means slidable in said channel and liquid-ingredient measuring and conveying means slidable in said guideway,
   a discharge port in said cover part,
   said assembly being movable from a normal position to a discharge position to deliver both the solid and the liquid ingredients into said discharge port,
   measuring means for said liquid ingredient comprising a transverse passage in said liquid ingredient measuring and conveying means providing a measuring chamber,
   a longitudinal passage in said liquid ingredient measuring and conveying means, one end of which connects with said measuring chamber,
   a valve member mounted for rectilinear slidable movement in said longitudinal passage to vary the volume of said measuring chamber,
   means movable relative to and engaging said valve member and manually operable in one direction to decrease the volume of said chamber for controlling the volume of said measuring chamber,
   means on said liquid ingredient conveying means to maintain said valve member in adjusted position, said body part having a recess receiving said means to maintain said valve member in adjusted position inaccessibly in normal position of said assembly, and
   said transverse passage connecting said liquid ingredient passage in the normal position and said discharge port in said discharge position.

8. A device as claimed in claim 7 in which said means movable relative to and engaging said valve member is a rectilinearly movable member having a cam surface engaging said valve member to move it.

9. A device as claimed in claim 7 in which said liquid ingredient measuring and conveying means includes a member which is cylindrical and has a slot at one end, and said means movable relative to and engaging said valve member is slidable rectilinearly.

10. A device as claimed in claim 9 having a member mounted on the slotted end of said dispensing member holding said rectilinearly movable member in said slot.

11. A device as claimed in claim 7 in which said liquid ingredient measuring and conveying means includes a member which is cylindrical and has a slot at one end, and said manually operable means is a rectilinearly movable member slidable in said slot, and a member mounted on the slotted end of said dispensing member holding said rectilinearly movable member in said slot.

12. A device as claimed in claim 7 in which said means to maintain said valve member in adjusted position is a nut member screw-threadedly mounted on said liquid ingredient measuring and conveying means.

* * * * *

When the slidable assembly is pushed from the position of FIG. 7 to the position of FIG. 8, it moves within and between the body head 22 and the cover head 32 beneath it, and the pellet aperture 42 with its pellet moves over an amalgam aperture 34 formed through the cover head 32 and drops through it into the capsule 18. At the same time and as a result of the same motion of the slide, a measured amount of mercury is deposited in the capsule through the same aperture 34 by a measuring and dispensing arrangement of the type disclosed in copending application of J. G. Biondo, Ser. No. 609,283, patented May 17, 1977 No. 4,023,715.

In the head 22 of the body part 20 is the aforementioned transverse cylindrical guideway 26 which passes directly under the mercury passage 25 and connects with it.

In the transverse guideway 26 is located the cylindrical measuring and dispensing rod 50 having in the midportion thereof a measuring chamber consisting of a radial bore 53 and cylindrical inlet and outlet openings 52', 52".

As previously stated, the dispensing assembly 40 is slidable from one position to another, i.e., from a measuring to a discharge position. In the measuring position, the mercury measuring chamber opening 52' is in alignment with the inlet port 25 to receive mercury from the cartridge 16. As the member moves to the discharge position, it conveys the mercury dosage in 52', 53, 52" to the discharge port 34 through which the mercury is delivered down gutter 35 to common discharge part 34.

In order to bias the dispensing assembly 40 normally into the measuring position, a coiled compression spring 56 is positioned around the dispensing rod 50 between the head 22 and the thumb piece 44.

In order to vary the volume of the measuring chamber with precision and accuracy, a slidable valve member designated generally by numeral 54, is provided within a bore in one end of the dispensing rod 50. The valve has a cylindrical stem 54s, which is slidably extensible into the axial bore 53 of the dispensing rod 50. The diameter of the bore 53 may, if desired, be larger than the diameter of the inlet and outlet parts 52', 52" of the measuring chamber to enlarge the central portion of the measuring chamber. The valve 54 has a dome-shaped head 54h which is located in the outer end of the rod 50. The inner end of the valve stem may be inserted variable amounts into the measuring chamber to vary the dosage which the chamber can accept. The valve 54 is normally biased by a coiled compression spring 55 coiled around its stem and pressing at one end against a shoulder on the valve 54 and at its other end against the end of the valve-containing bore in the dispensing rod 50.

To regulate and adjust the position of the valve 54, a manually operable cam member designated generally by 60, is slidably located in a diametrical slot 58 formed in the end of the dispensing member 50 adjacent the valve head. The cam member 60 has flat parallel sides 62, 63 (FIG. 13) extending between parallel end faces 64, 65 (FIG. 4) and a longitudinal flat cam face 66 and inclined between the ends 64, 65, with a lateral extension 65x at the end 65.

The head 54h of the valve member under urge of spring 55 is biased against the cam face 66. Movement of the cam member 60 in one direction is limited by the extension 65x from the side at the end 65. Another extension 69 for a similar purpose is provided at the end 64 (see FIG. 3).

The sliding action of the cam 60 moves the valve 54 axially, projecting its stem 54s into the chamber 53 the desired amount, thereby determining the amount of mercury or other material the chamber can receive.

To hold the cam member 60 in slot 58 in a predetermined position, a cylindrical cap member 59 is internally threaded and screwed over the open end of the dispensing member 50 until the periphery or rim of the open end of the cap, pressing against the straight surface of the cam member locates the cam member and valve in the desired position.

Preferably, the side face or faces of the cam member are marked with calibrations such as A to E and the edge of the cam may be providing with locating notches so that the dispensing member can be set for a desired mercury dosage by reference to the calibrations.

In order to lock the cam member in adjusted position, means are provided on the liquid ingredient conveying means to maintain the valve member (54 in the illustrated embodiment) in adjusted position, these means being provided in the illustrated embodiment by an externally knurled circular lock nut 70 screwed on the end of dispensing rod member 50 inwardly of the cap 59 and cam member 60. See FIGS. 6, 7 and 8. Because the inclined edge 66 of the cam member faces the flat radial surface of the lock nut, a cylindrical collar 72 having a diametrical slot is placed on the dispensing rod 50 between the cam member 60 and lock nut 70, with the slot in register with the slot 58 of the dispensing rod 50. The portion of slot 74' (see FIG. 4) which is engaged by the thicker part of the cam member is deeper than the portions 74" which is engaged by the thinner part of the cam member so that when the collar is pushed against the cam member, the latter is firmly held with straight line contact on both edges and cannot tilt.

In operation, the device is grasped in hand, palm down, and held in the position of FIG. 1. The slide assembly 50 will be located as shown in FIGS. 1, 7 and 13 with the pellet aperture 42 in register with the vial aperture 23 and the mercury inlet 53' in register with the mercury cartridge opening 24, and adjustment cam 60 will be along the slot 58 into the position which will provide the desired dosage.

The thumb piece 44 is then pushed and the dispensing assembly is slid to place the measuring chamber in register with the discharge port 34 for discharge of the measured amount from the measuring chamber down the gutter 35, to the common capsule opening 34 and into the capsule 18. Likewise the pellet aperture 42 will have moved over the common mercury and pellet discharge 34 so that the pellet will drop down into the capsule 18.

In order to prevent movement of the dispensing assembly 40 from measuring into discharge position with there is no capsule in position to catch the memory and pellet, a latch member 80 is provided to lock the assembly except when the capsule is in place. The latch member is a flat bifurcated member, preferably formed as shown in FIG. 5, and pivoted on a pin 84 which is located in a recess 28 (see FIGS. 10 and 11) in the inner face of the body 20. Aligned cooperating slots 27 and 36 transverse to the direction of movement of the slide assembly are formed in the body 20 and cover 30 to allow pivotal movement of the latch member. To bias the latch into locking position, a coiled compression spring 86 is seated in a circular hole in the body head 22